United States Patent [19]

Cavezzan et al.

[11] Patent Number: 5,340,898

[45] Date of Patent: Aug. 23, 1994

[54] CATIONICALLY CROSSLINKABLE POLYORGANOSILOXANES AND ANTIADHESIVE COATINGS PRODUCED THEREFROM

[75] Inventors: Jacques Cavezzan; Christian Priou, both of Villeurbanne, France

[73] Assignee: Rhone-Poulenc Chimie, Courbevoie, France

[21] Appl. No.: 35,603

[22] Filed: Mar. 23, 1993

[30] Foreign Application Priority Data

Mar. 23, 1992 [FR] France ............................ 92 03441

[51] Int. Cl.$^5$ ............................................. C08G 77/06
[52] U.S. Cl. ........................................ 528/19; 528/21; 528/23; 522/64; 522/65; 522/66; 522/67; 522/68; 428/447
[58] Field of Search ............................ 528/21, 23, 19; 428/447; 522/64, 65, 66, 67, 68

[56] References Cited

U.S. PATENT DOCUMENTS

| | | | |
|---|---|---|---|
| 4,576,999 | 3/1986 | Eckberg | 525/474 |
| 4,617,238 | 10/1986 | Crivello et al. | 528/23 |
| 4,640,967 | 2/1987 | Eckberg | 528/26 |

FOREIGN PATENT DOCUMENTS

| | | |
|---|---|---|
| 0353030A2 | 1/1990 | European Pat. Off. . |
| 0442635A1 | 8/1991 | European Pat. Off. . |
| 0464706A1 | 1/1992 | European Pat. Off. . |
| 2025469 | 12/1970 | Fed. Rep. of Germany . |

*Primary Examiner*—Melvyn I. Marquis
*Attorney, Agent, or Firm*—Burns, Doane, Swecker & Mathis

[57] ABSTRACT

Cationically crosslinkable polyorganosiloxane compositions, well suited for providing antiadhesive coatings on a wide variety of shaped substrates via the photochemical/electron beam crosslinking thereof, include a catalytically effective amount of an onium borate of an element of Groups 15 to 17 of the Periodic Table, the anionic borate moiety of which onium borate having the formula:

$$[BX_aR_b]^-$$

in which a and b are integers ranging from 0 to 4 and a+b=4; the symbols X are each a halogen atom when a ranges up to 3 and an OH functional group when a ranges up to 2; and the symbols R, which may be identical or different, are each a phenyl radical substituted by at least one electron-withdrawing substituent or by at least two halogen atoms, or an aryl radical containing at least two aromatic ring members, or such aryl radical bearing at least one electron-withdrawing substituent.

15 Claims, No Drawings

CATIONICALLY CROSSLINKABLE POLYORGANOSILOXANES AND ANTIADHESIVE COATINGS PRODUCED THEREFROM

BACKGROUND OF THE INVENTION

1. Field of the Invention

The present invention relates to compositions based on polyorganosiloxanes containing cationically crosslinkable functional groups and to the preparation of antiadhesive coatings therefrom, as well as final articles comprising a solid substrate, at least one face surface of which is rendered antiadhesive by coating same with such functional polyorganosiloxanes and then effecting the crosslinking thereof via photochemical activation or by an electron beam.

2. Description of the Prior Art

It is known to this art to prepare antiadhesive coating compositions based on a polyorganosiloxane containing functional groups (of the epoxy or vinyl ether type, and the like) to which an onium salt is added as a cationic initiator for the crosslinking thereof (U.S. Pat. Nos. 4,450,360, 4,576,999 and 4,640,967).

It has been observed that the best results are obtained using onium salts in which the anion is $SbF_6^-$; initiators containing this type of anion, however, present toxicity risks.

SUMMARY OF THE INVENTION

Accordingly, a major object of the present invention is the provision of novel compositions based on crosslinkable polyorganosiloxanes containing functional groups and an onium salt cationic crosslinking initiator therefor which comprises an anion exhibiting a nucleophilicity close to that of $SbF_6^-$, but without presenting the disadvantages associated therewith.

Briefly, the present invention features novel compositions based on a cationically crosslinkable polyorganosiloxane and a catalytically effective amount of an onium borate of an element selected from among Groups 15 to 17 of the Periodic Table [Chem. & Eng. News, Vol. 63, No. 5, 26; 4 February 1985]; the cationic moiety of said onium borate being selected from among:

(1) the onium salts having the formula (I):

$$[(R^1)_n-A-(R^2)_m]^+ \quad (I)$$

in which A is an element from Groups 15 to 17, such as I, S, Se, P, N and the like; $R^1$ is a $C_6$–$C_{20}$ heterocyclic or carbocyclic aryl radical, said heterocyclic radical containing at least one of the heteroelements, nitrogen, sulfur, and the like; $R^2$ is $R^1$ or a linear or branched, $C_1$–$C_{30}$ alkenyl or alkyl radical, said radicals $R^1$ and $R^2$ optionally being substituted by a $C_1$–$C_{25}$ alkoxy, $C_1$–$C_{25}$ alkyl, nitro, chloro, bromo, cyano, carboxyl, mercapto group and the like; n is an integer ranging from 1 to v+1, with v being the valence of the element A; and m is an integer ranging from 0 to v-1 with n+m=v1;

(2) the oxoisothiochromanium salts described in WO-A-90/11,303, especially the 2-ethyl-4-oxoisothiochromanium or 2-dodecyl-4-oxoisothiochromanium chromanium sulfonium salt;

and the anionic borate moiety having the formula:

$$[BX_aR_b]^-$$

in which a and b are integers ranging from 0 to 4 with a+b=4; the symbols X are each a halogen atom (chlorine or fluorine) with a=0 to 3, or an OH functional group with a=0 to 2; and the symbols R, which may be identical or different, are each a phenyl radical substituted by at least one electron-withdrawing group, such as $CF_3$, $NO_2$, $CN$ and the like, or by at least two halogen atoms (most particularly fluorine), or an aryl radical containing at least two aromatic ring members, such as biphenyl, naphthyl and the like, and optionally substituted by at least one electron-withdrawing element or group, especially a halogen atom (most particularly fluorine), $CF_3$, $NO_2$, $CN$ and the like.

DETAILED DESCRIPTION OF PREFERRED EMBODIMENTS OF THE INVENTION

More particularly according to the present invention, exemplary borate anions include:

$[B(C_6F_5)_4]^-$, $[B(C_6H_4CF_3)_4]^-$,
$[(C_6F_5)_2]^-$, $[C_6F_5BF_3]^-$, $[B(C_6H_3F_2)_4]^-$,

The onium salts having the formula (I) are described in the literature, patent and otherwise, for example in U.S. Pat. Nos. 4,026,705, 4,032,673, 4,069,056, 4,136,102 and 4,173,476.

The following cations, wherein $\Phi$ is phenyl, are very particularly representative:

$[(\Phi)_2I]^+$, $[C_8H_{17}-O-\Phi-I-\Phi]^+$, $[C_{12}H_{25}-\Phi-I-\Phi]^+$, $[(C_8H_{17}-O-\Phi)_2I]^+$, $[(\Phi)_3S]^+$, $[(\Phi)_2-S-\Phi-O-C_8H_{17}]^+$, $[\Phi-S-\Phi-S-(\Phi)_2]^+$, $[(C_{12}H_{25}-\Phi)_2I]^+$

And exemplary of the onium borates are the following:

$[(\Phi)_2I]^+$ $[B(C_6F_5)_4]^-$, $[C_{12}H_{25}-\Phi-I-\Phi]^+$ $[B(C_6F_5)_4]^-$, $[(C_8H_{17}-O-\Phi)_2I]^+$ $[B(C_6F_5)_4]^-$, $[(C_8H_{17})-O-\Phi-I-\Phi]^+$ $[B(C_6F_5)_4]^-$, $[(\Phi)_3S]^+$ $[B(C_6F_5)_4]^-$, $[(\Phi)_2S-\Phi-O-C_8H_{17}]^+$ $[B(C_6H_4CF_3)_4]^-$, $[(C_{12}H_{25}-\Phi)_2I]^+$ $[B(C_6F_5)_4]^-$.

The onium borates according to the present invention can be prepared by an exchange reaction between a salt of the cationic moiety, especially a halide (chloride, iodide), and an alkali metal salt (sodium, lithium or potassium) of the anionic moiety.

The operating conditions (respective amounts of reactants, choice of solvents, duration, temperature, stirring and the like) are easily determined by one skilled in this art; they must permit recovery of the desired initiator salt in the solid state, by filtration of the precipitate formed, or in the oily state, by extraction using a suitable solvent.

The alkali metal salts of the anionic moiety can be prepared in known manner, by an exchange reaction between a haloborated compound and an organometallic compound (of magnesium, lithium, tin and the like) bearing the desired hydrocarbon groups, in a stoichiometric amount, optionally followed by a hydrolysis using an aqueous solution of an alkali metal halide; this type of synthesis is, for example, described in *J. of Organometallic Chemistry*, Vol. 178, p. 1–4 (1979); *J.A.C.S.*, 82, 5298 (1960); *Anal. Chem. Acta*, 44, 175–183 (1969); U.S. Pat. No. 4,139,681 and DE-A-2,901,367;

*Zh. Org. Khim.*, Vol. 25, No. 5 —pages 1099–1102 (May 1989).

The cationically crosslinkable polyorganosiloxanes which comprise the compositions of the invention are substituted by functional groups of the epoxy or vinyl ether type, or the like.

Such polyorganosiloxanes are linear or substantially linear and comprise recurring structural units of formula (II) and endgroups of formula (III), or are cyclic and comprise recurring structural units of formula (II)

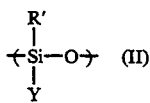 (II)   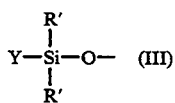 (III)

in which formulae the symbols R', which may be identical or different, are each a $C_1$–$C_6$ linear or branched alkyl radical, which is optionally substituted (3,3,3-trifluoropropyl, for example), a $C_5$–$C_8$ cycloalkyl radical, an aryl (especially phenyl) radical, a substituted aryl (dichlorophenyl, for example) radical and the like, at least 60 molar % of the radicals R' being methyl radicals; and the symbols Y which may be identical or different, are each a group R' or a cationically crosslinkable functional organic radical, such as the epoxyfunctional, vinyloxyfunctional and the like groups, said epoxide, vinyl ether and the like functional groups being bonded to an atom of the silicone chain via a divalent bridge having from 2 to 20 carbon atoms; with the proviso that at least one of the symbols Y is a cationically crosslinkable functional organic radical, and preferably from 1 to 10 functional organic radicals per mole of polymer.

The epoxy- or vinyloxyfunctional polyorganosiloxanes are described, especially, in DE-A-4,009,899, EP-A-396,130, EP-A-355,381, EP-A-105,341, FR-A-2,110,115 and FR-A-2,526,800.

The epoxyfunctional polyorganosiloxanes can be prepared by a hydrosilylation reaction between oils containing Si-H structural units and epoxyfunctional compounds such as 4-vinylcyclohexene oxide, allyl glycidyl ether and the like.

The vinyloxyfunctional polyorganosiloxanes can be prepared by a hydrosilylation reaction between oils containing Si-H structural units and vinyloxyfunctional compounds, such as allyl vinyl ether, allylvinyl-oxyethoxybenzene and the like.

The epoxy- or vinyloxyfunctional polyorganosiloxanes are generally provided in the form of fluids exhibiting a viscosity at 25° C. of 10 to 10,000 mm²/s and preferably from 100 to 600 mm²/s.

By "catalytically effective amount" of onium borate is intended that amount which is sufficient to initiate crosslinking; this amount generally ranges from 0.01 to 20 parts by weight, typically from 0.1 to 20 parts by weight, typically from 0.1 to 8 parts by weight, to crosslink photochemically 100 parts by weight of the crosslinkable polyorganosiloxane.

The compositions according to the invention can additionally contain other additives and adjuvants, such as adherence modulators (linear silicone polymers or resins bearing vinyl, epoxy, vinyl ether, alcohol and the like functional groups), pigments, photosensitizing agents, fungicidal, bactericidal and antimicrobial agents, corrosion inhibitors and the like.

The compositions according to the invention can be used as such or in solution in an organic solvent. They are useful for providing antiadherent coatings on cellulosic materials, films, paints, encapsulation of electrical and electronic components, coatings for textiles and for sheathing optical fibers.

They are very particularly advantageous when they are used, as such, to produce a material, such as metal sheets, glass, plastics or paper, that is nonadherent to other materials to which it would normally adhere. The composition advantageously exhibits a viscosity not exceeding 5,000 mPa.s, preferably not exceeding 4,000 mPa.s at 25° C.

Thus, the present invention also features a process for the production of articles (sheets for example) that are nonadherent to surfaces to which they normally adhere, comprising coating an amount of the subject composition, generally from 0.1 to 5 g per m², onto at least one face surface thereof, and crosslinking the composition by supplying energy, at least a part of which, preferably all, is provided by U.V. radiation.

The U.V. radiation used has a wavelength of from 200 to 400 nanometers, preferably from 254 to 360 nanometers.

The duration of irradiation can be short and it is generally less than 1 second and is on the order of a few hundreds of a second for very thin coatings. The crosslinking attained is excellent even in the absence of any heating. It will of course be appreciated that heating at a temperature of from 25° C. to 100° C. is also within the scope of the invention.

It will of course be appreciated that the hardening time, especially, can be adjusted, by the number of U.V. lamps used, by the duration of exposure to U.V. and by the distance between the composition and the U.V. lamp.

The solvent-free compositions, namely, undiluted, are applied with the aid of devices capable of uniformly depositing small amounts of liquids. For such purpose, for example, the device designated "Helio glissant" may be used, comprising, in particular, two superposed cylinders; the function of the lower-placed cylinder, immersed in the coating vat where the composition is situated, is to impregnate, in a very thin layer, the higher-placed cylinder. The function of the latter is then to deposit the desired amounts of composition with which it is impregnated onto the paper; such a uniform feeding is provided by adjusting the respective speeds of the two cylinders which rotate in opposite directions with respect to each other.

The amounts of compositions deposited onto the substrates are variable and typically range from 0.1 to 5 g/m² of treated surface. These amounts depend on the nature of the substrates and on the desired antiadherent properties. They usually range from 0.5 to 3 g/m² for nonporous substrates.

The present invention also features the final articles (sheets for example) comprising a solid material (metal, glass, plastic, paper, and the like), at least one face surface of which is coated with a composition as described above, which composition is photocrosslinked or crosslinked by an electron beam.

In order to further illustrate the present invention and the advantages thereof, the following specific examples are given, it being understood that same are intended only as illustrative and in nowise limitative.

EXAMPLE 1

Diphenyliodonium tetrakis(pentafluorophenyl)borate
[(Φ)$_2$I]+ [B(C$_6$F$_5$)$_4$]−

Preparation of lithium tetrakis(pentafluorophenyl)borate

A 4,000 ml, four-necked, round-bottom flask, equipped with a mechanical stirrer, a water-cooled reflux condenser, a thermometer and a dropping funnel, was employed. The assembly was dried beforehand under an argon atmosphere.

1,600 ml of anhydrous pentane and 126.8 g (or 0.513 mol) of bromopentafluorobenzene were charged therein. This medium was stirred and then cooled to −75° C. using a solid carbon dioxide/acetone bath.

313 ml of a 1.6M solution of n-butyllithium in hexane were charged into the dropping funnel and were then added dropwise over 50 minutes.

The mixture was maintained under stirring for 5 hours at a temperature of −78° C.

125 ml of a 1M solution of boron trichloride in hexane were charged into the dropping funnel and added to the mixture over thirty minutes. The cooling bath was removed and the reaction mixture was permitted to return to room temperature. It was then maintained under stirring for 12 hours. The reaction mixture was hydrolyzed by slow addition of 625 ml of water. The two phases were separated and the organic phase was washed with two 125 ml fractions of water. The aqueous phases were combined and were then extracted three times with ether (3×125 ml). The ether phases were combined and dried over magnesium sulfate. The ether was evaporated under reduced pressure and 101 g (or a yield of 99%) of lithium tetrakis(pentafluorophenyl)borate were recovered.

Preparation of diphenyliodonium tetrakis(pentafluorophenyl)borate 7.17 g (or 22.6 mmol) of diphenyliodonium chloride were dissolved in 300 ml of water in a 1,000 ml Erlenmeyer flask. 15.52 g (or 22.6 mmol) of lithium tetrakis(pentafluorophenyl)borate in solution in 250 ml of water were added dropwise. The mixture was maintained under stirring for 30 minutes and was then filtered. The filtrate was dried under reduced pressure (133 Pa) overnight with the exclusion of light. 16.33 g (or a yield of 75%) of diphenyliodonium tetrakis(pentafluorophenyl)borate were thus recovered.

EXAMPLE 2

(4-Octyloxyphenyl)phenyliodonium tetrakis(Dentafluorophenyl)borate
[(C$_8$H$_{17}$)—O—Φ-I-Φ)]+ [B(C$_6$F$_5$)$_4$]−

Preparation of octyl phenyl ether:

44.8 g (or 0,477 mol) of phenol, 38.6 g (or 0.2 mol) of n-bromooctane, 6 g of tetrabutylammonium bromide, 26.8 g of potassium hydroxide, 100 ml of water and 100 ml of toluene were charged into a 500 ml, threenecked, round-bottom flask equipped with a mechanical stirrer, a thermometer and water-cooled reflux condenser. This medium was stirred and was then heated to reflux for 20 hours. The reaction mixture was then cooled to room temperature. The phases were settled and separated. The organic phase was washed with 100 ml of a 0.5N sodium hydroxide solution and then with five 100 ml fractions of water. It was then dried over magnesium sulfate and the solvent was then driven off under reduced pressure at a temperature of 85° C.

41.5 g (or a yield of 95%) of n-octyl phenyl ether, which could be used subsequently without additional purification, were recovered.

Preparation of hydroxytosyloxyiodobenzene 80.53 g (or 0.25 mol) of iodobenzene diacetate, 300 ml of water and 100 ml of acetic acid were charged into a 1,000 ml, round-bottom flask equipped with a mechanical stirrer, a water-cooled reflux condenser and a dropping funnel. This medium was stirred and was heated to 40° C. 47.55 g (or 0.25 mol) of paratoluenesulfonic acid monohydrate were then added over five minutes via the dropping funnel. The reaction mixture was maintained at 40° C. for two hours and was then cooled to 25° C. A white precipitate appeared. It was recovered by filtration and was then dried under reduced pressure.

68.15 g (or a yield of 70%) of the desired product were obtained.

Preparation of (4-octyloxyphenyl) phenyliodonium tosylate 22.2 g (or 0.057 mol) of hydroxytosyloxy-iodobenzene, 9 g (or 0.04 mol) of n-octyl phenyl ether, 5 ml of acetonitrile and 1.5 ml of acetic acid were charged into a 250 ml Erlenmeyer flask equipped with a magnetic stirrer bar. This mixture was stirred and was heated to a temperature of 40° C. for 2 hours and 30 minutes. 1.5 ml of glacial acetic acid were then added and the mixture was then maintained for 5 hours at 40° C. The reaction mixture was permitted to cool and 150 ml of water were added while stirring vigorously. This mixture was then stirred for 12 hours at room temperature and was then separated. The organic phase was washed several times with water, until a yellow precipitate appeared. This solid was recovered by filtration, was washed with 50 ml of ether and was then dried under vacuum at a temperature of 45° C.

19.5 g (or a yield of 76%) of (4-octyloxyphenyl)-phenyliodonium tosylate were thus recovered.

Preparation of (4-octyloxyphenyl)phenyliodonium tetrakis(pentafluorophenyl)borate 5 g (or 0.0086 mol) of (4-octyloxyphenyl)-phenyliodonium tosylate were dissolved in 350 ml of acetone in a 500 ml Erlenmeyer flask equipped with a magnetic stirrer bar. While light was excluded, 3.4 g (or 0.0103 mol) of lithium tetrakis(pentafluorophenyl)borate in solution in 50 ml of acetone were added. The mixture was stirred for 48 hours and was then filtered to remove the lithium p-toluenesulfonate formed. The acetone was evaporated under reduced pressure and 7.98 g (or a yield of 92%) of (4-octyloxyphenyl)phenyliodonium tetrakis(pentafluorophenyl)borate were recovered.

EXAMPLE 3

Bis (dodecylphenyl) iodonium tetrakis (pentafluorophenyl)-borate [(C$_{12}$H$_{25}$—Φ)$_2$I]+ [B(C$_6$F$_5$)$_4$]−

Preparation of bis(dodecylphenyl)iodonium chloride 100 g (or 0.405 mol) of dodecylbenzene, 43.5 g (or 0.203 mol) of potassium iodate, 199.6 g of acetic acid and 59.5 g of acetic anhydride were charged into a 1,000 ml, round-bottom flask equipped with a mechanical stirrer, a water-cooled reflux condenser and a dropping funnel. The mixture was stirred and then cooled in an ice bath to 0° C. A mixture of 59.8 g of sulfuric acid and 39.86 g of acetic acid was charged into the dropping funnel. This mixture was added to the reaction mixture over 25 minutes. The reaction mixture was maintained under stirring for 18 hours at room temperature. 750 ml of water were then added and the reaction mixture was then extracted with three ether fractions (3×350 ml). The ether phases were combined and then evaporated under reduced pressure. The concentrate was taken up in 540 ml of a saturated sodium chloride solution, and the mixture was then cooled in an ice bath for two hours. The product was recovered by filtration on sintered glass No. 4. The solid was then recrystallized twice from acetone. 69.18 g (or a yield of 52%) of bis(dodecylphenyl)iodonium chloride were recovered by filtration.

Preparation of bis(dodecylphenyl)iodonium tetrakis (pentafluorophenyl) borate 3.76 g of bis(dodecylphenyl)iodonium chloride were dissolved in 500 ml of acetone in a 1,000 ml Erlenmeyer flask. A solution of 5 g of lithium tetrakis(pentafluorophenyl)borate in 100 ml of acetone was then added dropwise. The mixture was maintained under stirring for two days, with the exclusion of light, and the lithium chloride formed was then removed by filtration. 8 g (or a yield of 90%) of bis(dodecylphenyl)iodonium tetrakis(pentafluorophenyl)borate were recovered after evaporation of the acetone.

EXAMPLES 4 to 10

The general procedure was the following:

(i) to 100 parts by weight of a polymer A, i.e., an organopolysiloxane containing trimethylsilyl endgroups and containing epoxide functional groups, were added:

(ii) 0.5 part by weight of photoinitiator as a 2% by weight solution in a solvent (methanol or 2-ethylhexanediol).

After manual stirring for 30 minutes, the mixture was deposited (approximately 0.5 to 3 g/m²) onto a Terphane ®6868 film (marketed by Rhône-Poulenc) having a thickness of 45 μm.

The coated film was transported under a U.V. lamp of the Fusion system ®F 450 type (marketed by Fusion) and characterized by:

(1) a wavelength of 360 nm,
(2) an absence of electrodes,
(3) excitation by microwaves,
(4) a power of 120 W per cm irradiated.

After passing under the lamp at the rate of 32 m/min, the irradiation energy was 0.025 J/cm² (measured with a Uvicure ® cell from Eit-USA); the winding speed in m/min required for hardening the silicone layer was recorded.

The quality of the coating obtained after hardening was evaluated by measuring the antiadherent properties of the silicone layer after having been placed in contact:

(a) for 20 hours at 20° C. with a rubber adhesive (Tesa 4154 and Tesa 4651) according to the FINAT No. 3 test, (b) for 20 hours at 70° C. with an acrylic adhesive (Tesa 4970) according to the FINAT No. 10 test.

Moreover, subsequent adhesion (SA) expresses the level of polymerization of the silicone layer. Measurement was carried out according to the FINAT No. 11 test.

The results obtained by using:

IN EXAMPLES 4 AND 5 (COMPARATIVE)

(i) a polyorganosiloxane $A_1$ of formula $MD^E_4D_{40}M$ wherein $M=(CH_3)_3SiO_{1/2}$, $D^E=$(4-cyclohexene oxide)$(CH_3)SiO_{2/2}$ and $D=(CH_3)_2SiO_{2/2}$ containing 104 meq/100 g of epoxide functional groups and having a viscosity of 600 mm²/s at 25° C., and (ii) a photoinitiator $B_1$, i.e., bis(dodecylphenyl)iodonium hexafluoroantimonate in solution in 2-ethylhexanediol.

IN EXAMPLES 6 TO 8

(i) a polyorganosiloxane $A_1$ and (ii) a photoinitiator $B_2$, i.e., diphenyliodonium tetrakis (pentafluorophenyl) borate in solution in methanol.

IN EXAMPLES 9 AND 10

(i) a polyorganosiloxane $A_2$ of formula $MD^E_4D_{30}M$ where M, $D^E$ and D are as defined above, containing 128 meq/100 g of epoxide functional groups and having a viscosity of 500 mm²/s at 25° C., and (ii) the photoinitiator $B_2$, are reported in the following Table:

TABLE

| Example | Speed (m/min) | Quantity deposited (g/m²) | Antiadherence (g/cm) | | | SA (%) |
|---|---|---|---|---|---|---|
| | | | Tesa 4154 20 h at 20° C. | Tesa 4651 20 h at 20° C. | Tesa 4970 20 h at 70° C. | |
| 4 | 100 | 1.0 | 1.4 | 6.0 | 65 | 78 |
| 5 | 130 | 1.2 | 1.5 | 6.9 | 43 | 75 |
| 6 | 100 | 1.1 | 1.6 | 9.2 | 17 | 86 |
| 7 | 130 | 0.9 | 1.8 | 10 | 22 | 80 |
| 8 | 150 | 0.7 | 1.7 | 9.7 | 37 | 95 |
| 9 | 100 | 1.2 | 30 | 56 | 55 | 86 |
| 10 | 190 | 1.0 | 16 | 45 | 76 | 96 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter comprising a cationically crosslinkable polyorganosiloxane and a catalytically effective amount of an onium borate of an element of Groups 15 to 17 of the Periodic Table, the anionic borate moiety of which onium borate having the formula:

$$[BX_aR_b]^-$$ 

in which a is an integer ranging from 0 to 3, b is an integer ranging from 0 to 4 and a+b=4; the symbols X are each a halogen atom when a ranges up to 3 and an OH functional group when a ranges up to 2; and the symbols R, which may be identical or different, are each a phenyl radical substituted by at least one electron-withdrawing substituent or by at least two halogen atoms, or an aryl radical containing at least two aromatic ring members, or such aryl radical bearing at least one electron-withdrawing substitutent.

2. The polyorganosiloxane composition as defined by claim 1, the cationic moiety of which onium borate having the formula (I):

$$[(R^1)_n\text{—A—}(R^2)_m]^+ \quad (I)$$

in which A is an element of Groups 15 to 17 of the Periodic Table; $R^1$ is a $C_6$-$C_{20}$ heterocyclic or carbocyclic aryl radical; $R^2$ is $R^1$ or a linear or branched $C_1$-$C_{30}$ alkenyl or alkyl radical, or such alkenyl or alkyl radical bearing at least one $C_1$-$C_{25}$ alkoxy, $C_1$-$C_{25}$ alkyl, nitro, chloro, bromo, cyano, carboxyl or mercapto substituent; n is an integer ranging from 1 to v+1, with v being the valence of the element A; and m is an integer ranging from 0 to v−1, with the proviso that n+m=v+1.

3. The polyorganosiloxane composition as defined by claim 1, the cationic moiety of which onium borate comprising that of an oxoisothiochromanium salt.

4. The polyorganosiloxane composition as defined by claim 1, wherein said anionic borate moiety, said at least one electron-withdrawing substituent comprises $CF_3$, $NO_2$, CN or at least one halogen atom.

5. The polyorganosiloxane composition as defined by claim 2, wherein said cationic moiety having the formula (I), A is I, S, Se, P or N.

6. The polyorganosiloxane composition as defined by claim 3, said oxoisothiochromanium salt comprising 2-ethyl-4-oxoisothiochromanium or 2-dodecyl-4-oxoisothiochromanium sulfonium salt.

7. The polyorganosiloxane composition as defined by claim 1, said anionic borate moiety having one of the formulae:

$[B(C_6F_5)_4]^-$, $[B(C_6H_4CF_3)_4]^-$, $[(C_6F_5)_2BF_2]^-$, $[C_6F_5BF_3]^-$ or $[B(C_6H_3F_2)_4]^-$.

8. The polyorganosiloxane composition as defined by claim 2, said cationic onium moiety having one of the formulae:

$[(\Phi)_2I]^+$, $[C_8H_{17}\text{—O-}\Phi\text{-I-}\Phi]^+$, $[C_{12}H_{25}\text{-}\Phi\text{-I-}\Phi]^+$, $[(C_8H_{17}\text{—O-}\Phi)_2I]^+$, $[(\Phi)_3S]^+$, $[(\Phi)_2\text{-S-}\Phi\text{-O—}C_8H_{17}]^+$, $[\Phi\text{-S-}\Phi\text{-S-}(\Phi)_2]^+$ or $[(C_{12}H_{25}\text{-}\Phi)_2I]^+$, in which $\Phi$ is phenyl.

9. The polyorganosiloxane composition as defined by claim 1, said onium borate having one of the formulae:

$[(\Phi)_2I]^+$ $[B(C_6F_5)_4]^-$, $[C_{12}H_{25}\text{-}\Phi\text{-I-}\Phi]^+$ $[B(C_6F_5)_4]^-$, $[(C_8H_{17}\text{—O-}\Phi)_2I]^+$ $[B(C_6F_5)_4]^-$, $[(C_8H_{17})\text{—O-}\Phi\text{-I-}\Phi]^+$ $[B(C_6F_5)_4]^-$, $[(\Phi)_3S]^+$ $[B(C_6F_5)_4]^-$, $[(\Phi)_2S\text{-}\Phi\text{-O—}C_8H_{17}]^+$ $[B(C_6H_4CF_3)_4]^-$ or $[(C_{12}H_{25}\text{-}\Phi)_2I]^+$ $[B(C_6F_5)_4]^-$, in which $\Phi$ is phenyl.

10. The polyorganosiloxane composition as defined by claim 1, said cationically crosslinkable polyorganosiloxane having epoxy or vinyl ether functional groups.

11. The polyorganosiloxane composition as defined by claim 1, said cationically crosslinkable polyorganosiloxane having a viscosity at 25° C. ranging from about 10 to 10,000 mm²/s.

12. The polyorganosiloxane composition as defined by claim 1, in crosslinked elastomeric state.

13. A shaped substrate bearing a coating of the polyorganosiloxane composition as defined by claim 1 on at least one face surface thereof.

14. A shaped substrate bearing an antiadherent coating of the crosslinked polyorganosiloxane composition as defined by claim 12 on at least one face surface thereof.

15. The shaped article as defined by claim 13, comprising from 0.1 to 5 g of said polyorganosiloxane composition per m² of coated surface of said substrate.

* * * * *